(12) United States Patent
Girdhar et al.

(10) Patent No.: US 11,918,242 B2
(45) Date of Patent: Mar. 5, 2024

(54) RETRIEVAL OF MATERIAL FROM VESSEL LUMENS

(71) Applicant: Covidien LP, Mansfield, MA (US)

(72) Inventors: Gaurav Girdhar, Ladera Ranch, CA (US); Hoai Nguyen, Westminster, CA (US); Andyanhdzung Huynh, Westminster, CA (US)

(73) Assignee: COVIDIEN LP, Mansfield, MA (US)

( * ) Notice: Subject to any disclaimer, the term of this patent is extended or adjusted under 35 U.S.C. 154(b) by 343 days.

(21) Appl. No.: 17/249,438

(22) Filed: Mar. 2, 2021

(65) Prior Publication Data

US 2022/0280172 A1 Sep. 8, 2022

(51) Int. Cl.
*A61B 17/221* (2006.01)
*A61B 17/00* (2006.01)

(52) U.S. Cl.
CPC .. *A61B 17/221* (2013.01); *A61B 2017/00017* (2013.01)

(58) Field of Classification Search
CPC .......... A61B 2018/0041; A61B 17/221; A61B 2017/00017; A61B 2017/00154; A61B 17/22031; A61B 2017/2215
See application file for complete search history.

(56) References Cited

U.S. PATENT DOCUMENTS

| 10,835,268 | B2* | 11/2020 | Wallace | ......... A61B 17/320725 |
| 2014/0277013 | A1* | 9/2014 | Sepetka et al. | |
| 2020/0390458 | A1 | 12/2020 | Nguyen et al. | |

FOREIGN PATENT DOCUMENTS

| EP | 2967605 A1 | 1/2016 | |
| WO | WO-2012049652 A1 * | 4/2012 | ....... A61B 17/22031 |
| WO | 2016198947 A1 | 12/2016 | |
| WO | 2019246377 A2 | 12/2019 | |

OTHER PUBLICATIONS

International Search Report and Written Opinion dated May 17, 2022; International Application No. PCT/US2022/014486; 15 pages.

* cited by examiner

Primary Examiner — Julian W Woo
(74) Attorney, Agent, or Firm — Fortem IP LLP; Candice Hsu; Suzannah Beeman

(57) ABSTRACT

Retrieval of material from vessel lumens can be improved by electrically enhancing attachment of the material to the thrombectomy system. The system can include a catheter having a distal portion configured to be positioned adjacent to a thrombus in a blood vessel, an electrode disposed at the distal portion of the catheter, and an interventional element configured to be delivered through a lumen of the catheter. The electrode and the interventional element are each configured to be electrically coupled to an extracorporeal power supply. The interventional element may be configured to evert over and around the clot material while current is delivered to the interventional element.

20 Claims, 7 Drawing Sheets

RETRIEVAL OF MATERIAL FROM VESSEL LUMENS

TECHNICAL FIELD

The present technology relates generally to devices and methods for removing obstructions from body lumens. Some embodiments of the present technology relate to devices and methods for removal of clot material from blood vessels.

BACKGROUND

Many medical procedures use medical device(s) to remove an obstruction (such as clot material) from a body lumen, vessel, or other organ. An inherent risk in such procedures is that mobilizing or otherwise disturbing the obstruction can potentially create further harm if the obstruction or a fragment thereof dislodges from the retrieval device. If all or a portion of the obstruction breaks free from the device and flows downstream, it is highly likely that the free material will become trapped in smaller and more tortuous anatomy. In many cases, the physician will no longer be able to use the same retrieval device to again remove the obstruction because the device may be too large and/or immobile to move the device to the site of the new obstruction.

Procedures for treating ischemic stroke by restoring flow within the cerebral vasculature are subject to the above concerns. The brain relies on its arteries and veins to supply oxygenated blood from the heart and lungs and to remove carbon dioxide and cellular waste from brain tissue. Blockages that interfere with this blood supply eventually cause the brain tissue to stop functioning. If the disruption in blood occurs for a sufficient amount of time, the continued lack of nutrients and oxygen causes irreversible cell death. Accordingly, it is desirable to provide immediate medical treatment of an ischemic stroke.

To access the cerebral vasculature, a physician typically advances a catheter from a remote part of the body (typically a leg) through the abdominal vasculature and into the cerebral region of the vasculature. Once within the cerebral vasculature, the physician deploys a device for retrieval of the obstruction causing the blockage. Concerns about dislodged obstructions or the migration of dislodged fragments increases the duration of the procedure at a time when restoration of blood flow is paramount. Furthermore, a physician might be unaware of one or more fragments that dislodge from the initial obstruction and cause blockage of smaller more distal vessels.

Many physicians currently perform thrombectomies (i.e. clot removal) with stents to resolve ischemic stroke. Typically, the physician deploys a stent into the clot in an attempt to push the clot to the side of the vessel and re-establish blood flow. Tissue plasminogen activator ("tPA") is often injected into the bloodstream through an intravenous line to break down a clot. However, it takes time for the tPA to reach the clot because the tPA must travel through the vasculature and only begins to break up the clot once it reaches the clot material. tPA is also often administered to supplement the effectiveness of the stent. Yet, if attempts at clot dissolution are ineffective or incomplete, the physician can attempt to remove the stent while it is expanded against or enmeshed within the clot. In doing so, the physician must effectively drag the clot through the vasculature, in a proximal direction, into a guide catheter located within vessels in the patient's neck (typically the carotid artery). While this procedure has been shown to be effective in the clinic and easy for the physician to perform, there remain some distinct disadvantages to using this approach.

For example, one disadvantage is that the stent may not sufficiently retain the clot as it pulls the clot to the catheter. In such a case, some or all of the clot might remain in the vasculature. Another risk is that, as the stent mobilizes the clot from the original blockage site, the clot might not adhere to the stent as the stent is withdrawn toward the catheter. This is a particular risk when passing through bifurcations and tortuous anatomy. Furthermore, blood flow can carry the clot (or fragments of the clot) into a branching vessel at a bifurcation. If the clot is successfully brought to the end of the guide catheter in the carotid artery, yet another risk is that the clot may be "stripped" or "sheared" from the stent as the stent enters the guide catheter.

In view of the above, there remains a need for improved devices and methods that can remove occlusions from body lumens and/or vessels.

SUMMARY

Mechanical thrombectomy (i.e., clot-grabbing and removal) has been effectively used for treatment of ischemic stroke. Although most clots can be retrieved in a single pass attempt, there are instances in which multiple attempts are needed to fully retrieve the clot and restore blood flow through the vessel. Additionally, there exist complications due to detachment of the clot from the interventional element during the retrieval process as the interventional element and clot traverse through tortuous intracranial vascular anatomy. For example, the detached clot or clot fragments can obstruct other arteries leading to secondary strokes. The failure modes that contribute to clot release during retrieval are: (a) boundary conditions at bifurcations; (b) changes in vessel diameter; and (c) vessel tortuosity, amongst others.

Certain blood components, such as platelets and coagulation proteins, display negative electrical charges. The systems of the present technology provide an interventional element and a current generator configured to positively charge the interventional element during one or more stages of a thrombectomy procedure. For example, the current generator may apply a constant or pulsatile direct current (DC) to the interventional element. The positively charged interventional element attracts negatively charged blood components, thereby improving attachment of the thrombus to the interventional element and reducing the number of device passes or attempts necessary to fully retrieve the clot. In some aspects of the present technology, the system includes an interventional element configured to evert over the clot material, thereby encapsulating the clot material during retrieval.

The present technology is illustrated, for example, according to various aspects described below. Various examples of aspects of the present technology are described as numbered clauses (1, 2, 3, etc.) for convenience. These are provided as examples and do not limit the present technology. It is noted that any of the dependent clauses may be combined in any combination, and placed into a respective independent clause, e.g., clause (1, 15, 25, 34, etc.). The other clauses can be presented in a similar manner.

1. A medical device comprising:
   an elongate member having a proximal end portion and a distal end portion configured to be positioned proximate a thrombus within a lumen of a blood vessel at a treatment site; and a mesh having a first end portion coupled to the distal end portion of the elongate member and a second end portion, wherein the mesh has an expanded state in which the mesh is eversible between first and second positions, and wherein the mesh is configured to be electrically coupled to an electrical terminal that delivers a current to the mesh to positively charge the mesh and promote adhesion of the thrombus thereto, wherein, when the device is positioned within the blood vessel lumen and the mesh is in the first position of the expanded state, proximal movement of the elongate member causes the mesh to move from the first position towards the second position.

2. The device of any one of the previous Clauses, wherein:
the elongate member is a first elongate member,
the electrical terminal is a first electrical terminal and is configured to be coupled to the proximal end portion of the first elongate member, and
the device further comprises a second elongate member having a proximal end region configured to be coupled to a second electrical terminal and a distal end region configured to be positioned adjacent the mesh at the treatment site.

3. The device of Clause 2, wherein the first electrical terminal is positive and the second electrical terminal is negative.

4. The device of Clause 2 or Clause 3, wherein, when the mesh is in the presence of an electrolytic medium and voltage is supplied to the first and second electrical terminals, current flows from the mesh to the second elongate member.

5. The device of any one of the previous Clauses, wherein the mesh is in electrical communication with the elongate member.

6. The device of any one of the previous Clauses, wherein the mesh comprises a plurality of braided metallic wires.

7. The device of any one of the previous Clauses, wherein, when the mesh is in the first position, at least a portion of a length of the mesh surrounds a portion of the elongate member.

8. The device of any one of the previous Clauses, wherein, when the mesh is in the second position, most of a length of the mesh is distal of the elongate member.

9. The device of any one of the previous Clauses, wherein, when the mesh is in the second position, an entire length of the mesh is distal of the elongate member.

10. The device of any one of the previous Clauses, wherein the mesh is closed at the first end portion and open at the second end portion.

11. The device of any one of the previous Clauses, wherein the first end portion of the mesh is fixed relative to the elongate member and the second end portion is free to move relative to the elongate member.

12. The device of any one of the previous Clauses, wherein a portion of the mesh is coated with a non-conductive material.

13. The device of any one of the previous Clauses, wherein the elongate member comprises an electrically conductive member configured to carry electrical current between the first electrical terminal and the mesh.

14. The device of Clause 13, wherein the elongate member further comprises an insulative material at least partially surrounding the electrically conductive member.

15. The device of Clause 13 or 14, wherein the electrically conductive member comprises a wire or a hypotube.

16. The device of any one of the previous Clauses, wherein the mesh comprises a generally tubular structure.

17. The device of any one of the previous Clauses, wherein the mesh comprises a sidewall that surrounds an interior lumen.

18. The device of any one of the previous Clauses, wherein the first end portion of the mesh is fixedly attached to a distal end of the elongate member.

19. The device of any one of the previous Clauses, wherein the first end portion of the mesh is closed.

20. The device of any one of the previous Clauses, wherein the first end portion of the mesh is gathered together at the elongate member.

21. The device of any one of the previous Clauses, wherein the second end portion of the mesh is open.

22. A medical device comprising:
a first elongate member having a proximal region configured to be coupled to a first electrical terminal and a distal region configured to be positioned adjacent a thrombus in a blood vessel;
a second elongate member having a proximal end portion configured to be coupled to a second electrical terminal and a distal end portion; and
a mesh having a first end portion coupled to the distal end portion of the second elongate member and a second end portion, the mesh being movable between (a) a first position in which the second end portion is proximal of the first end portion, and (b) a second position in which the second end portion is distal of the first end portion.

23. The device of any one of the previous Clauses, wherein the mesh is in electrical communication with the second elongate member.

24. The device of any one of the previous Clauses, wherein the first elongate member is an elongate shaft defining a lumen and the second elongate member is configured to be slidably received within the lumen.

25. The device of any one of the previous Clauses, wherein the first electrical terminal is positive and the second electrical terminal is negative.

26. The device of any one of the previous Clauses, wherein, when the mesh is in the presence of an electrolytic medium and voltage is supplied to the first and second electrical terminals, current flows from the mesh to the first elongate member.

27. The device of any one of the previous Clauses, wherein a portion of the mesh is coated with a non-conductive material.

28. The device of any one of the previous Clauses, wherein the mesh comprises a plurality of braided metallic wires.

29. The device of any one of the previous Clauses, wherein, when the mesh is in the first position, at least a portion of a length of the mesh surrounds a portion of the second elongate member.

30. The device of any one of the previous Clauses, wherein, when the mesh is in the second position, most of a length of the mesh is distal of the second elongate member.

31. The device of any one of the previous Clauses, wherein the mesh is closed at the first end portion and open at the second end portion.

32. A method for retrieving clot material from within a vessel lumen of a patient, the method comprising:
positioning a mesh within the vessel lumen at or near the clot material, the mesh having a first end portion coupled to an elongate member and a second end portion;
expanding the mesh within the vessel lumen into a first position such that at least a portion of the mesh expands into contact with the clot material, wherein the first end portion of the mesh is distal of the second end portion of the mesh when the mesh is in the first position;

promoting adhesion of the clot material to the mesh by delivering an electrical signal to the mesh; and pulling the elongate member proximally, thereby transforming the mesh into a second position in which the second end portion of the mesh is distal of the first end portion such that the mesh encapsulates at least a portion of the clot material.

33. The method of any one of the previous Clauses, further comprising ceasing delivery of the electrical current to the mesh after a time period.

34. The method of any one of the previous Clauses, wherein the time period is less than about 5 minutes.

35. The method of any one of the previous Clauses, wherein the time period is less than about 2 minutes.

36. The method of any one of the previous Clauses, wherein the electrical signal is positively charged.

37. The method of any one of the previous Clauses, wherein the electrical signal is delivered to the mesh while the elongate member pulls the mesh proximally.

38. The method of any one of the previous Clauses, wherein the mesh is in electrical communication with the elongate member.

39. The method of any one of the previous Clauses, further comprising withdrawing the mesh and the at least a portion of the clot material from the patient.

40. The method of any one of the previous Clauses, wherein the mesh is any of the meshes disclosed herein.

41. A method for retrieving clot material from within a vessel lumen of a patient, the method comprising:

positioning a mesh within the vessel lumen at or near the clot material, the mesh having a first end portion coupled to an elongate member and a second end portion;

expanding the mesh within the vessel lumen into a first position in which the first end portion of the mesh is distal of the second end portion of the mesh, wherein at least a portion of the clot material is positioned between the mesh and the vessel wall;

promoting adhesion of the clot material to the mesh by delivering an electrical signal to the mesh; and pulling the elongate member proximally to evert the mesh into a second position in which the second end portion of the mesh is distal of the first end portion and the at least a portion of the clot material is positioned within an interior cavity defined by the mesh.

42. The method of any one of the previous Clauses, further comprising ceasing delivery of the electrical current to the mesh after a time period.

43. The method of any one of the previous Clauses, wherein the time period is less than about 5 minutes.

44. The method of any one of the previous Clauses, wherein the time period is less than about 2 minutes.

45. The method of any one of the previous Clauses, wherein the electrical signal is positively charged.

46. The method of any one of the previous Clauses, wherein the electrical signal is delivered to the mesh while the elongate member pulls the mesh proximally.

47. The method of any one of the previous Clauses, wherein the mesh is in electrical communication with the elongate member.

48. The method of any one of the previous Clauses, further comprising withdrawing the mesh and the at least a portion of the clot material from the patient.

49. The method of any one of the previous Clauses, wherein the mesh is any of the meshes disclosed herein.

Additional features and advantages of the present technology are described below, and in part will be apparent from the description, or may be learned by practice of the present technology. The advantages of the present technology will be realized and attained by the structure particularly pointed out in the written description and claims hereof as well as the appended drawings.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

DETAILED DESCRIPTION

I. Select Embodiments of Systems

Figure 1:
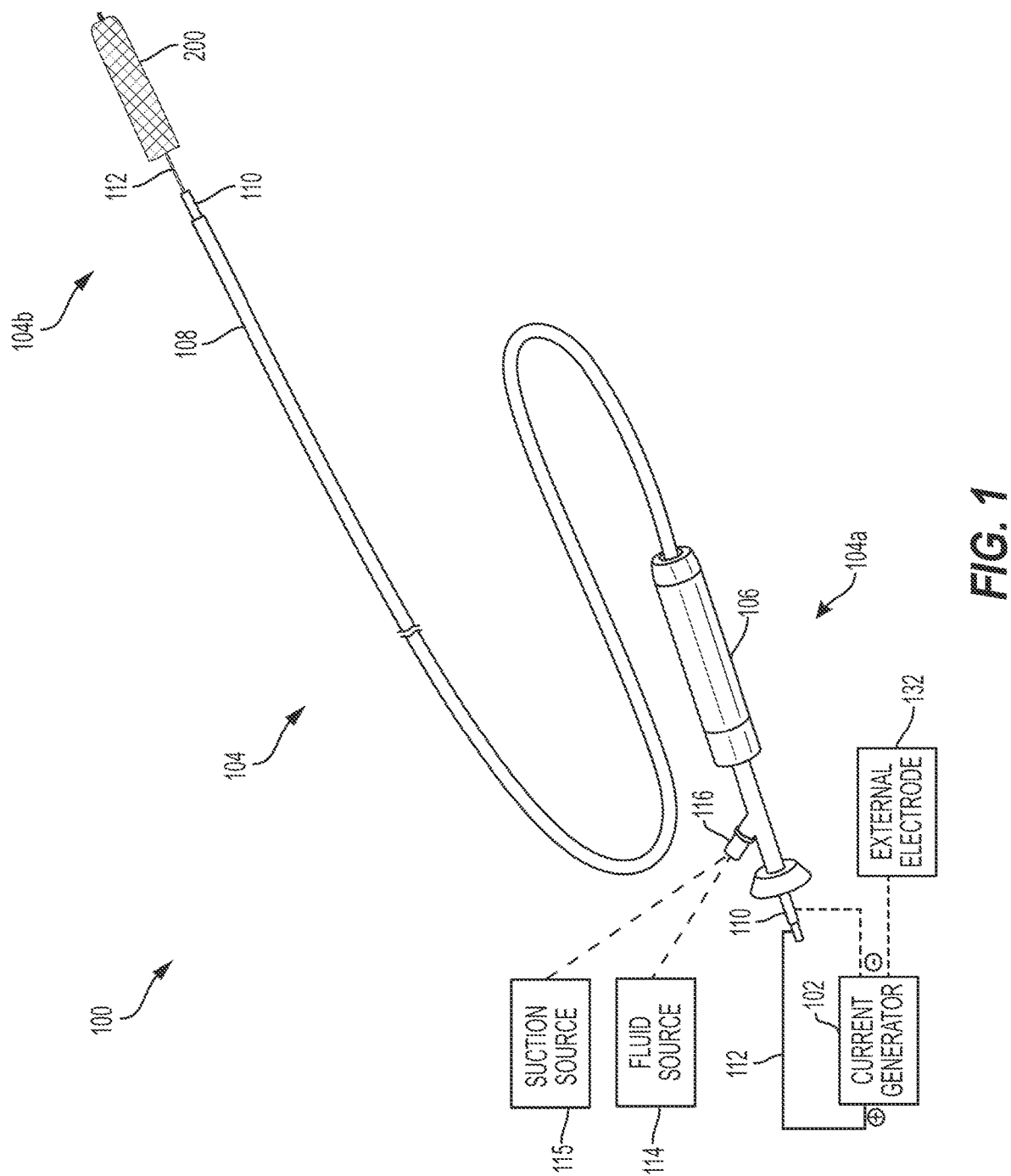
FIG. 1 shows a perspective view of a system for retrieving material from a body lumen, in accordance with one or more embodiments of the present technology.

FIG. 1 illustrates a system 100 for removing material from a vessel lumen according to one or more embodiments of the present technology. As shown in FIG. 1, the system 100 can include a current generator 102 and a treatment device 104 having a proximal portion 104a configured to be coupled to the current generator 102 and a distal portion 104b configured to be intravascularly positioned within a blood vessel (such as an intracranial blood vessel) at a treatment site at or proximate a thrombus. The treatment device 104 may include an interventional element 200 at the distal portion 104b, a handle 106 at the proximal portion 104a, and one or a plurality of elongate members extending therebetween. In some embodiments, for example as shown in FIG. 1, the treatment device 104 includes a first catheter 108 (such as a guide catheter), a second catheter 110 (such as a microcatheter) configured to be slidably disposed within a lumen of the first catheter 108, and an elongate member 112 configured to be slidably disposed within a lumen of the second catheter 110. The elongate member 112 has a distal portion coupled to the interventional element 200 and is configured to push and pull the interventional element 200 along the vasculature. In some embodiments, the system 100 optionally includes a third catheter, such as a distal access catheter or aspiration catheter (not shown). The third catheter may be configured to be slidably disposed within a lumen of the first catheter 108, and has a lumen configured to receive the second catheter 110 therethrough. As described herein, the current generator 102 is configured to be coupled to a proximal portion of one or more of the elongate member 112, the first catheter 108, the second catheter 110, and/or the third catheter to provide an electrically charged environment at the distal portion 104*b* of the treatment device 104 to promote adhesion of the thrombus to the interventional element 200.

Figure 2:
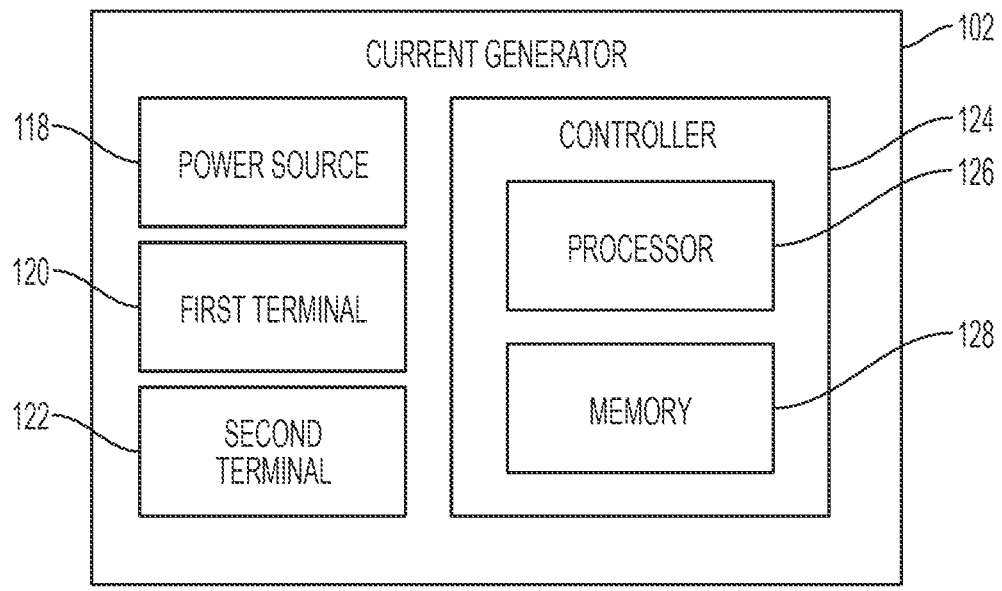
FIGS. 2 and 3 are schematic views of different embodiments of the current generator of FIG. 1.
Figure 3:
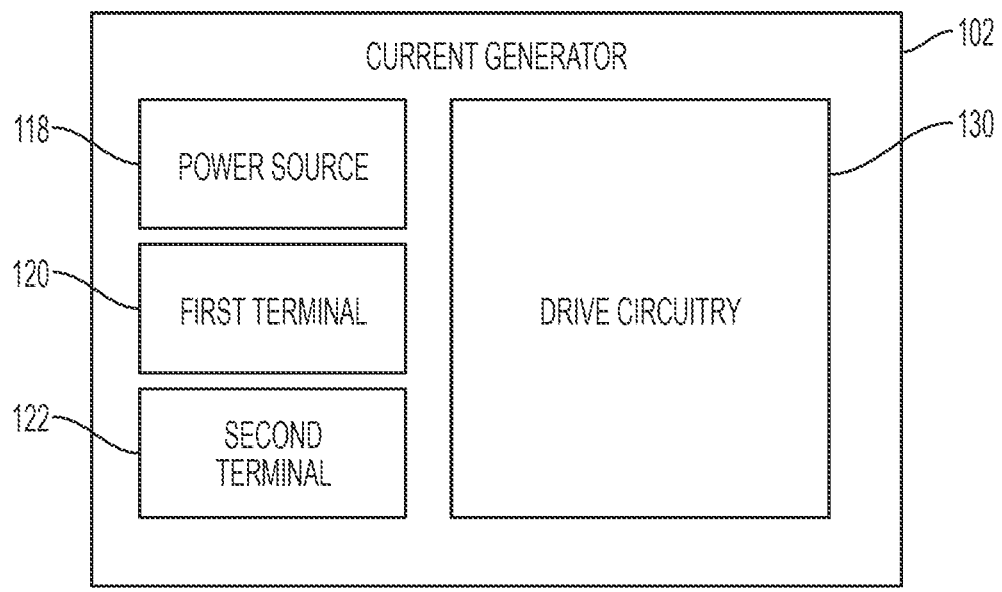

According to some embodiments, the current generator 102 can include an electrical generator configured to output medically useful electric current. FIGS. 2 and 3 are schematic views of different embodiments of the current generator 102. With reference to FIG. 2, the current generator 102 can include a power source 118, a first terminal 120, a second terminal 122, and a controller 124. The controller 124 includes a processor 126 coupled to a memory 128 that stores instructions (e.g., in the form of software, code or program instructions executable by the processor or controller) for causing the power source 118 to deliver electric current according to certain parameters provided by the software, code, etc. The power source 118 of the current generator 102 may include a direct current power supply, an alternating current power supply, and/or a power supply switchable between a direct current and an alternating current. The power source may therefore comprise a battery, transformer, rectifier, a connection to electrical mains or service grid, or any other suitable source of AC or DC electrical power. The current generator 102 can include a suitable controller that can be used to control various parameters of the energy output by the power source or generator, such as intensity, amplitude, duration, frequency, duty cycle, and polarity. For example, the current generator 102 can provide a voltage of about 2 volts to about 28 volts and a current of about 0.5 mA to about 20 mA. In some embodiments, the current generator 102 is configured to deliver current to the interventional element 200 for about 1 minute to about 5 minutes, about 1 minute to about 3 minutes, or at least 2 minutes.

FIG. 3 illustrates another embodiment of the current generator 102, in which the controller 124 of FIG. 2 is replaced with drive circuitry 130. In this embodiment, the current generator 102 can include hardwired circuit elements to provide the desired waveform delivery (or a constant current) rather than a software-based generator of FIG. 2. The drive circuitry 130 can include, for example, analog circuit elements (e.g., resistors, diodes, switches, etc.) that are configured to cause the power source 118 to deliver electric current via the first and second terminals 120, 122 according to the desired parameters. For example, the drive circuitry 130 can be configured to cause the power source 118 to deliver periodic waveforms via the first and second terminals 120, 122.

Referring again to FIG. 1, the first and second catheters (and third catheter when included) can each be formed as a generally tubular member extending along and about a central axis and terminating at a respective distal end. The first catheter 108 may be a balloon-guide catheter having an inflatable balloon or other expandable member (e.g., at or near the distal end thereof) that can be used to anchor the first catheter 108 with respect to a surrounding vessel. In some embodiments, the first catheter 108 does not include an expandable member. The second catheter 110 may be generally constructed to track over a conventional guidewire in the cervical anatomy and into the cerebral vessels associated with the brain. The second catheter 110, for example, can have a length that is at least 125 cm long, and more particularly may be between about 125 cm and about 175 cm long. Other designs and dimensions are contemplated. The third catheter, if included, can be sized and configured to be slidably receive the second catheter 110 therethrough.

According to some embodiments, the bodies of the catheters can be made from various thermoplastics, e.g., polytetrafluoroethylene (PTFE or TEFLON®), fluorinated ethylene propylene (FEP), high-density polyethylene (HDPE), polyether ether ketone (PEEK), etc., which can optionally be lined on the inner surface of the catheters or an adjacent surface with a hydrophilic material such as polyvinylpyrrolidone (PVP) or some other plastic coating. Additionally, either surface can be coated with various combinations of different materials, depending upon the desired results.

As shown in FIG. 1, the system 100 may additionally include a suction source 115 (e.g., a syringe, a pump, etc.) configured to be fluidly coupled (e.g., via a connector 116) to a proximal portion of one or more of the first catheter 108, the second catheter 110, and/or the third catheter to apply negative pressure therethrough. In these and other embodiments, the system 100 includes a fluid source 114 (e.g., a fluid reservoir, a syringe, pump, etc.) configured to be fluidly coupled (e.g., via the connector 116) to a proximal portion of one or more of the first catheter 108, the second catheter 110, and/or the third catheter to supply fluid (e.g., saline, contrast agents, a drug such as a thrombolytic agent, etc.) to the treatment site.

Figure 4:
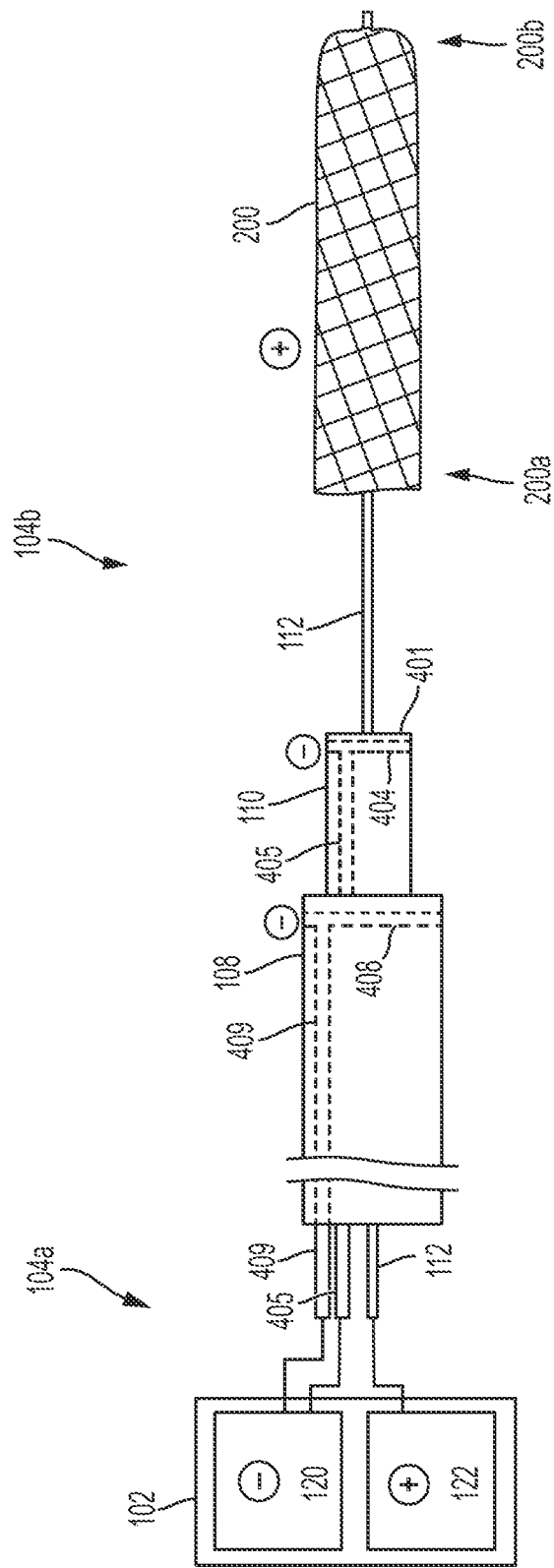
FIG. 4 is a side schematic view of the proximal and distal portions of the system of FIG. 1.

FIG. 4 is a side schematic view of the proximal and distal portions 104*a*, 104*b* of the treatment device 104 shown in FIG. 1. As shown in FIG. 4, in some embodiments the first terminal 120 of the current generator 102 is coupled to one or more of the catheters and the second terminal 122 is coupled to a proximal portion of the elongate member 112. The elongate member 112 can include an elongate conductive shaft in electrical communication with the current generator 102 and the interventional element 200. In some embodiments, the elongate conductive shaft can be covered with an electrically insulative material along at least a portion of its length. The elongate member 112 and the interventional element 200 together may comprise a delivery electrode or conductive path (i.e., transmitting current from the current generator 102 to the treatment site) while one or more of the catheters may provide a negative electrode or conductive path (i.e., transmitting current from the treatment site to the current generator 102). In some embodiments, the negative electrode can be provided via one or more external electrodes 132 (FIG. 1), such as a needle puncturing the patient or a grounding pad applied to the patient's skin. In some embodiments, the negative electrode can be an insulated guide wire having an exposed, electrically conductive portion at its distal end.

As shown in FIG. 4, the first terminal 120 may be negatively charged and the second terminal 122 may be positively charged such that, when voltage is applied at the terminals and the interventional element 200 is placed in the presence of blood (or any other electrolytic medium), current flows from the interventional element 200, through the blood or medium, and to the negative electrode(s). Positive current delivered to the interventional element 200 can attract negatively charged constituents of the clot material, thereby enhancing the grip of the interventional element 200 on the clot material. This enables the interventional element 200 to be used to retrieve the clot material with reduced risk of losing grip on the thrombus or a piece thereof, which can migrate downstream and cause additional vessel blockages in areas of the brain that are more difficult to reach.

According to some embodiments, an electrode 404 is provided at a distal end region of the second catheter 110. The electrode 404 can form an annular ring that extends entirely circumferentially about the central axis of the second catheter 110. Alternatively or in combination, the electrode 404 can extend less than entirely circumferentially around the second catheter 110. For example, the electrode 404 may be entirely disposed on one radial side of the central axis. By further example, the electrode 404 may provide a plurality of discrete, noncontiguous electrode sections about the central axis. Such sections of the electrode 404 can be in electrical communication with a common conductive path so as to function collectively as a single electrode, or with multiple separate such paths to allow the sections to function independently if desired. The electrode 404 can be a band, a wire, or a coil embedded in the wall of the second catheter 110. According to some embodiments, the electrode 404 can be longitudinally separated from the distal end 401 of the second catheter 110 by a non-conductive portion of the second catheter 110. Alternatively, a distal portion of the electrode 404 can extend to the distal end 401 of the second catheter 110, such that the electrode 404 forms a portion of the distal end 401. According to some embodiments, an inner surface of the electrode 404 can be flush with an inner surface of the second catheter 110. Alternatively or in combination, the inner surface of the electrode 404 can extend more radially inwardly relative to the inner surface of the second catheter 110 (e.g., providing a "step"). Alternatively or in combination, the inner surface of the electrode 404 can extend less radially inwardly relative to the inner surface of the second catheter 110 (e.g., be recessed into the body). According to some embodiments, the electrode 404 can be surrounded radially by an outer section of the second catheter 110 to provide insulation from an external environment. In some embodiments, an outer surface of the electrode 404 can be flush with an outer surface of the second catheter 110 and can provide an exposed, radially outwardly facing electrode surface. In such instances, a radially inner section of the second catheter 110 can provide insulation from the environment within the lumen of the second catheter 110.

The electrode 404 can include one or more rings, one or more coils or other suitable conductive structures, and can each form at least one surface (e.g., an inner surface or an outer surface) that is exposed and configured for electrical activity or conduction. The electrode 404 can have a fixed inner diameter or size, or a radially expandable inner diameter or size. In some embodiments, the electrode 404 is a deposited or "painted" electrode. The electrode can include platinum, platinum alloys (e.g., 92% platinum and 8% tungsten, 90% platinum and 10% iridium), gold, cobalt-chromium, stainless steel (e.g., 304 or 316), nitinol, and combinations thereof, or any suitable conductive materials, metals or alloys.

In some embodiments, the electrode 404 can be a separate expandable member coupled to an outer surface of the second catheter 110, for example a braid, stent, or other conductive element coupled to an outer surface of the distal portion of the second catheter 110. In some embodiments, the electrode can be part of a flow-arrest element such as an expandable braid coupled to an occlusion balloon.

According to some embodiments, the electrode 404 can be electrically connected to the current generator 102 via a conductive lead 405. The conductive lead 405 can extend proximally along or within the wall of the second catheter 110 to or beyond the proximal end of the second catheter 110. The conductive lead 405 can include one or more than one conductive path extending within the walls of the second catheter 110. According to some embodiments, the conductive lead 405 can form a helical coil along or within at least a portion of the second catheter 110. Alternatively or in combination, the conductive lead 405 can form a braided, woven, or lattice structure along or within at least a portion of the second catheter 110. In some embodiments, the conductive lead 405 can be a conductive element (e.g., a wire, coil, etc.) wrapped around an external surface of the second catheter 110. In such instances, the conductive lead 405 can be coated with an insulative material along at least a portion of its length. The insulative material can be, for example, Parylene, PTFE, or other suitable insulative material.

Instead of or in addition to the second catheter 110, the first catheter 108 may be configured to provide a conductive return path. For example, a distal end region of the first catheter 108 may include an electrode 408 electrically connected to the current generator 102 via a conductive lead 409 which extends proximally along the first catheter 108. The configuration of the electrode 408 and the corresponding conductive lead 409 can be similar to any of the variations described above with respect to the electrode 404 and the conductive lead 405 of the second catheter 110.

In some embodiments, the third catheter (not shown) can be similarly equipped with corresponding electrodes instead of or in addition to the first catheter 108, the second catheter 110, and/or the elongate member 112. For example, the third catheter may include an electrode disposed at a distal end region of the third catheter. The electrode can be electrically connected to the current generator 102 via a conductive lead which extends proximally along the third catheter. The configuration of the electrode and the corresponding conductive lead can be similar to any of the variations described above with respect to the electrode 404 and the conductive lead 405 of the second catheter 110.

In various embodiments, the system can include any combination of the electrodes of the first, second, and third catheters described above. For example, the system may include the electrode 404 and the corresponding conductive lead 405 of the second catheter 110, while the third catheter and the first catheter 108 may be provided with no electrodes or conductive leads. In some embodiments, the system 100 may only include the electrode of the third catheter, while the second catheter 110 and the first catheter 108 may be provided with no electrodes or conductive leads. In some embodiments, the system 100 may include only the electrode 408 of the first catheter 108, while the second catheter 110 and the third catheter are provided with no electrodes or corresponding conductive leads. In those embodiments including only the first and second catheters 108, 110, either one of the first or second catheter can be provided with electrode(s) and corresponding lead(s), while the remaining catheter may have no electrode or conductive lead. In those embodiments including three catheters, any two of the first, second, and third catheters can be provided with electrodes and corresponding leads, while the remaining catheter may have no electrode or conductive lead.

In some embodiments, both terminals of the current generator 102 are configured to be electrically coupled to the elongate member 112 such that the elongate member 112 functions as both the delivery electrode or conductive path and the return electrode or conductive path. Examples of such embodiments can be found in PCT Application No. PCT/US19/38206, filed Jun. 20, 2019, which is incorporated by reference herein in its entirety. In some embodiments, the elongate member 112 can be insulated along at least a portion of its length, with exposed portions permitting electrical communication with the current generator 102 and the interventional element 200.

In certain embodiments, the polarities of the current generator 102 can be switched, so that the negative terminal is electrically coupled to the elongate member 112 and the positive terminal is electrically coupled to one or more of the catheters. This can be advantageous when, for example, attempting to attract predominantly positively charged material to the interventional element 200, or when attempting to break up a clot rather than grasp it with an interventional element. In some embodiments alternating current (AC) signals may be used rather than DC. In certain instances, AC signals may advantageously help break apart a thrombus or other material.

Figure 5A:
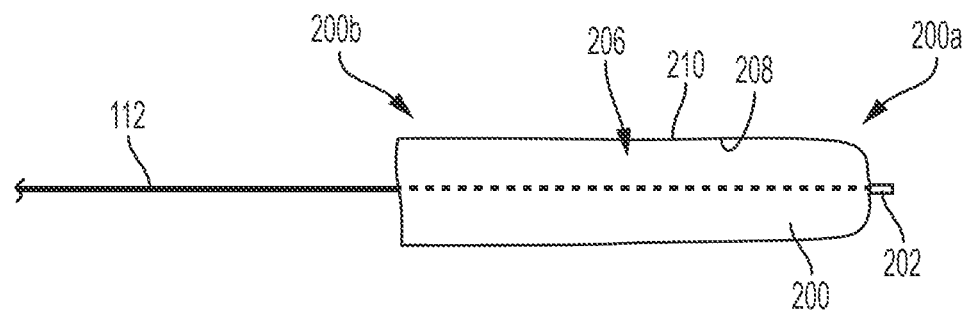
FIGS. 5A-5C illustrate the interventional element of the system of FIG. 1 in different positions in accordance with one or more embodiments of the present technology.
Figure 5B:
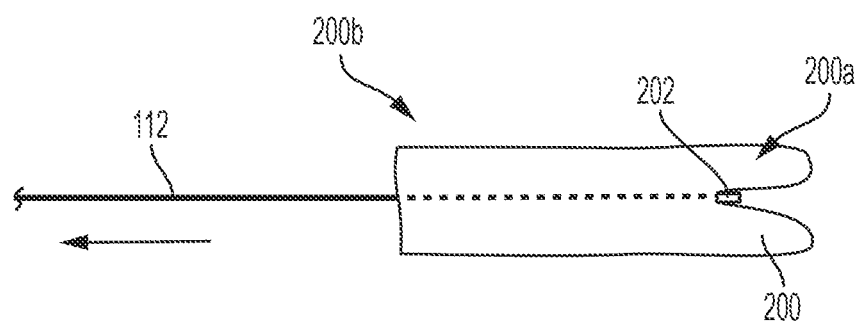
Figure 5C:
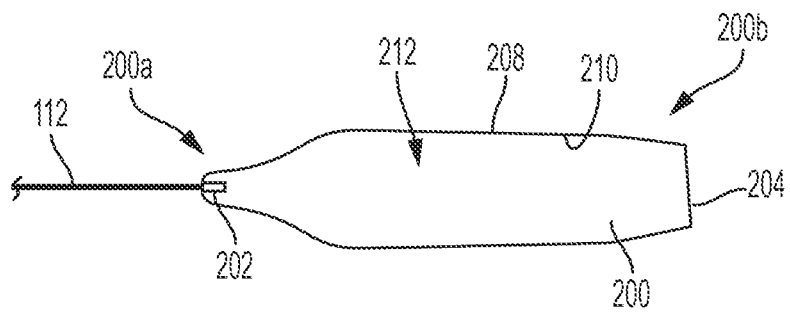

II. Select Embodiments of Interventional Elements for Use with the Systems Disclosed Herein FIGS. 5A-5C are side views of the interventional element 200 in different treatment positions in accordance with the present technology. The interventional element 200 can have a low-profile, constrained or compressed configuration (not shown) for intravascular delivery to the treatment site within the second catheter 110, and an expanded configuration for securing and/or engaging clot material and/or for restoring blood flow at the treatment site. When the interventional element 200 is first positioned within a blood vessel at a treatment site and allowed to expand, the interventional element 200 assumes a first position, as shown in FIG. 5A. Proximal movement of the elongate member 112 while the interventional element 200 is engaging the blood vessel walls causes the interventional element 200 to evert at a first end portion 200a, as depicted by the intermediate configuration of the interventional element in FIG. 5B. FIG. 5C shows the interventional element 200 in a fully everted, second position for removal from the body.

In some embodiments, for example as shown in FIGS. 5A-5C, the interventional element 200 comprises a generally tubular, self-expanding, eversible mesh 200 having a first end portion 200a coupled to the elongate member 112 via a connection assembly 202, a free second end portion 200b, and a sidewall extending between the first end portion 200a and the second end portion 200b. As used herein to describe the second end portion 200b of the mesh 200, the term "free" refers to a portion of the mesh 200 that is not fixed to the elongate member 112 and may move radially and/or longitudinally with respect to the elongate member 112. The mesh 200 is flexible such that it is movable between the first position (FIG. 5A) in which the free second end portion 200b is proximal of the first end portion 200a and a second position (FIG. 5C) in which the mesh 200 is everted such that the free second end portion 200b and/or a distal terminus 204 of the mesh 200 is at or distal to the distal terminus of the elongate member 112, the connection assembly 202, and/or the first end portion 200a. In the first position, the mesh 200 defines a first interior region 206 with a first surface 208 of the mesh 200 facing the interior region 206 and a second surface 210 of the mesh 200 facing away from the interior region 206 (towards the vessel wall). In the second position, the mesh 200 defines a second interior region 212 with the second surface 210 facing the interior region 212 and the first surface 208 facing away from the interior region 212 (towards the vessel wall). In some embodiments, the interventional element 200 can comprise the any of the embodiments of the eversible cover described in U.S. Pat. No. 8,795,305, filed on Aug. 5, 2013 (including the cover referred to by reference numeral 300 in the aforementioned '305 patent).

Figure 6A:
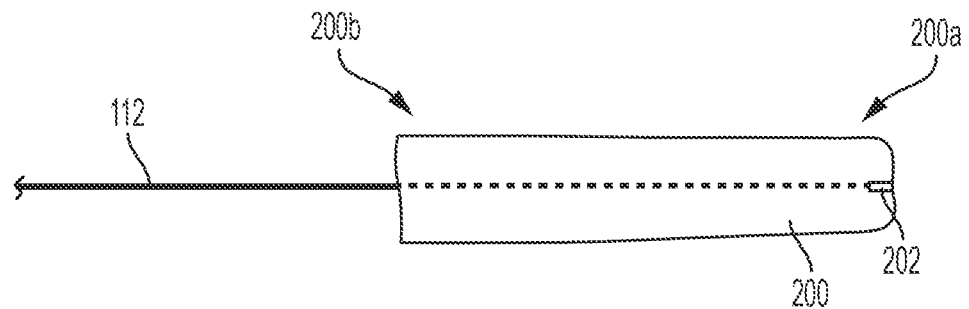
FIGS. 6A and 6B illustrate an interventional element in different positions in accordance with one or more embodiments of the present technology.
Figure 6B:
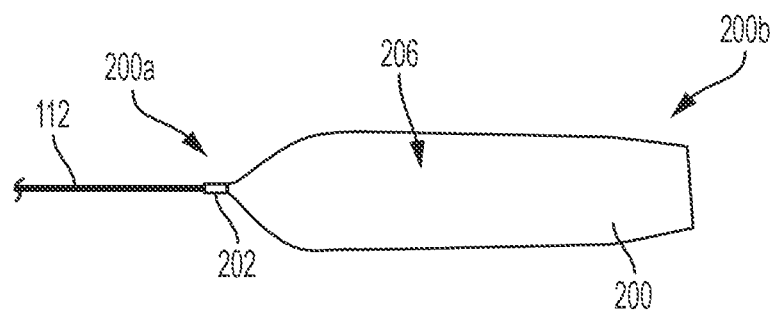

In some embodiments, the first end portion 200a of the mesh 200 extends away from a proximal end of the connection assembly 202. As a result, when the mesh 200 is in the second, everted position (FIG. 5C), the mesh 200 surrounds the connection assembly 202. In other embodiments, such as the interventional element 200 shown in FIG. 6A, the first end portion 200a of the mesh 200 extends from a distal end of the connection assembly 202 such that, when the mesh 200 is in the second, everted position (FIG. 6B), the entire mesh 200 is distal of the connection assembly 202.

All or a portion of the mesh 200 can comprise an electrically conductive material. In some embodiments, the mesh 200 comprises a braid formed of a plurality of wires (e.g., filaments, threads, sutures, fibers or the like) that have been interwoven to form a structure having openings. The mesh and/or braid can be composed of metals, polymers, composites, and/or biologic materials. Polymer materials can include Dacron, polyester, polypropylene, nylon, Teflon, polytetrafluoroethylene (PTFE), tetrafluoroethylene, polyethylene terephthalate, polyactic acid (PLA) silicone, polyurethane, polyethylene, polycarbonate, styrene, polyimide, PEBAX, Hytrel, polyvinyl chloride, high-density polyethylene, low-density polyethylene, polyether ether ketone (PEEK), rubber, latex, and/or other suitable polymers known in the art. Other materials known in the art of elastic implants can also be used. Metal materials can include, but are not limited to, nickel-titanium alloys (e.g. Nitinol), platinum, cobalt-chromium alloys, stainless steel, tungsten or titanium. In certain embodiments, metal filaments may be highly polished and/or surface treated to further improve their hemocompatibility. The mesh 200 can be constructed solely from metallic materials without the inclusion of any polymer materials, or a combination of polymer and metallic materials. The mesh and the pores thereof can be configured to permit blood or other liquids (e.g. saline, contrast solution, water, thrombolytic agents) to flow through.

In some embodiments, some or all of the wires of the mesh 200 are drawn-filled tube ("DFT") wires having a radiopaque core (e.g., platinum, tantalum, gold, tungsten, etc.) surrounded by a superelastic material (e.g., Nitinol, a cobalt-chromium alloy, etc.). The radiopaque core may comprise about 5% to about 50% (e.g., 10%, 15%, 20%, 25%, 30%, 35%, 40%, 45%) of the total-cross-sectional area of the individual wires. In some embodiments, the mesh 200 may have 16-144 total wires (e.g., 16, 32, 48, 72, 96, 128, 144, etc.). Moreover, some or all of the wires may have a wire diameter of about 0.0005 inches to about 0.0030 inches, or about 0.0008 inches to about 0.0020 inches. In some embodiments, all of the wires have the same diameter, and in other embodiments some of the wires have different diameters.

Figure 7:
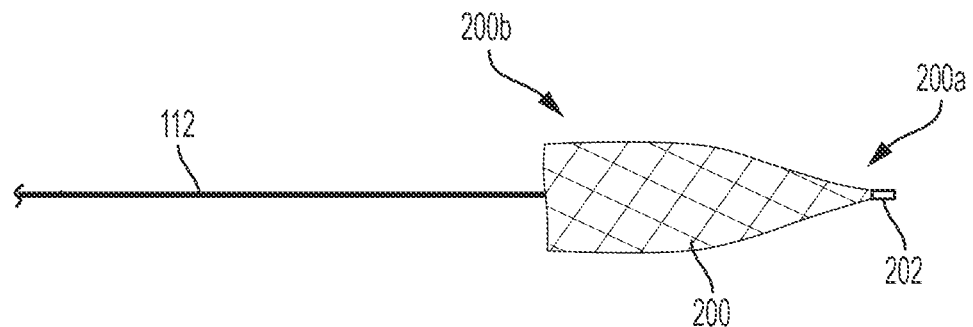
FIG. 7 illustrates an interventional element in a first position in accordance with one or more embodiments of the present technology.

In some embodiments, the mesh 200 may comprise a resilient material configured to self-expand when released from the second catheter 110. In some embodiments, the mesh 200 may have a preset and/or heat-set shape such that the mesh 200 assumes a predetermined shape in the first and/or second positions. In some embodiments, for example, the mesh 200 may be heat set to have a predetermined shape in the second position such that at least a portion of the length of the mesh tapers radially inwardly, thereby enclosing associated clot material and preventing or otherwise reducing the escape of particles from an interior region of the mesh 200. In some embodiments, for example as shown in FIG. 7, the mesh 200 may be heat set to have a predetermined shape in the first position such that a diameter of the mesh 200 increases in the direction of the second end portion 200b (i.e., tapers in the direction of the first end portion 200a). In some embodiments, the mesh 200 has a generally constant diameter along its length in the first position and/or second position.

The systems and methods of the present technology can further improve adhesion of the clot to the interventional element by varying features of the interventional element. For example, in some embodiments, some or all of the interventional element can be coated with one or more highly conductive materials, such as gold, to improve clot adhesion. In some aspects of the present technology, a working length of the interventional element may be coated with the conductive material while a non-working length of the interventional element may be coated with an insulative material. In any case, a portion of the interventional element may be coated with an insulative material.

In some embodiments, the system 100 further includes a capture structure (not shown) carried by a distal portion of the elongate member 112 and positioned distal of the interventional element 200. The capture structure may have a low-profile configuration (not shown) when constrained within the second catheter 110 and an expanded configuration for securing and/or engaging clot material or other obstructions within a blood vessel lumen (e.g., a cerebral blood vessel lumen) and/or for restoring blood flow within the blood vessel. The capture structure can have a proximal portion coupled to the elongate member 112 and a distal portion. The capture structure may comprise an open cell framework or body and a coupling region extending proximally from the body. In some embodiments, a distal portion of the capture structure can be generally tubular (e.g., cylindrical), and the proximal portion of the capture structure tapers proximally to the coupling region. In some embodiments, the capture structure is a mesh structure formed of a superelastic material (e.g., Nitinol) or other resilient or self-expanding material configured to self-expand when released from the delivery catheter. For example, in some embodiments the capture structure may be a stent and/or stentriever, such as Medtronic's Solitaire™ Revascularization Device, Stryker Neurovascular's Trevo® ProVue™ Stentriever, or other suitable devices. In other embodiments, the capture structure may include a plurality of braided filaments. Examples of suitable capture structures include any of those disclosed in U.S. Pat. No. 7,300,458, filed Nov. 5, 2007, U.S. Pat. No. 8,940,003, filed Nov. 22, 2010, U.S. Pat. No. 9,039,749, filed Oct. 1, 2010, and U.S. Pat. No. 8,066,757, filed Dec. 28, 2010, each of which is incorporated by reference herein in its entirety.

III. Select Methods of Use

Figure 8A:
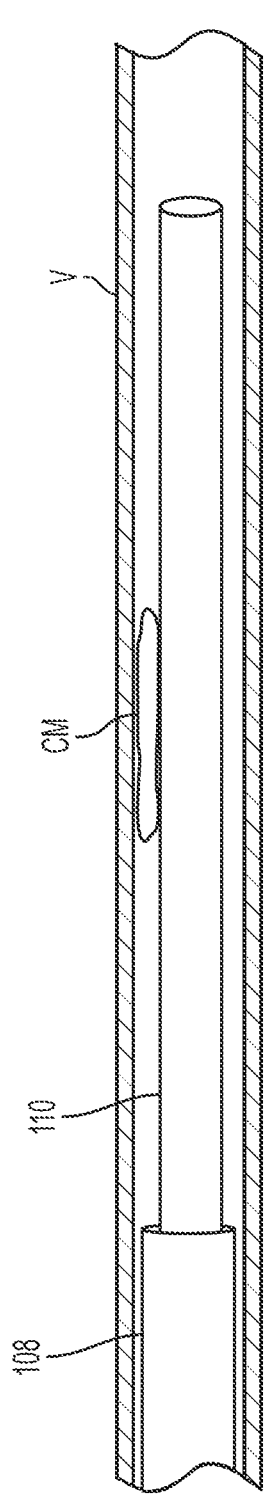
FIGS. 8A-8D illustrate a method of removing clot material from a blood vessel lumen using a system in accordance with one or more embodiments of the present technology.

The following will provide a description of the use of the interventional element 200 to remove clot material from a blood vessel. In use, the first catheter 108 can be advanced through the vasculature and positioned within the blood vessel such that a distal portion of the first catheter 108 is proximal of the clot material. If used, the third catheter may be advanced through the first catheter 108 until a distal portion of the third catheter is at or proximal to the clot material. Next, as shown in FIG. 8A, the second catheter 110 may be advanced through the first catheter 108 (and/or the third catheter) so that a distal portion of the second catheter 110 is positioned at or near the clot material CM. In some embodiments, the second catheter 110 may be positioned such that a distal terminus of the second catheter 110 is distal of the clot material CM. The interventional element 200 may then be advanced through the second catheter 110 in a low-profile configuration until a distal terminus of the interventional element 200 is at or adjacent the distal terminus of the second catheter 110.

Figure 8B:
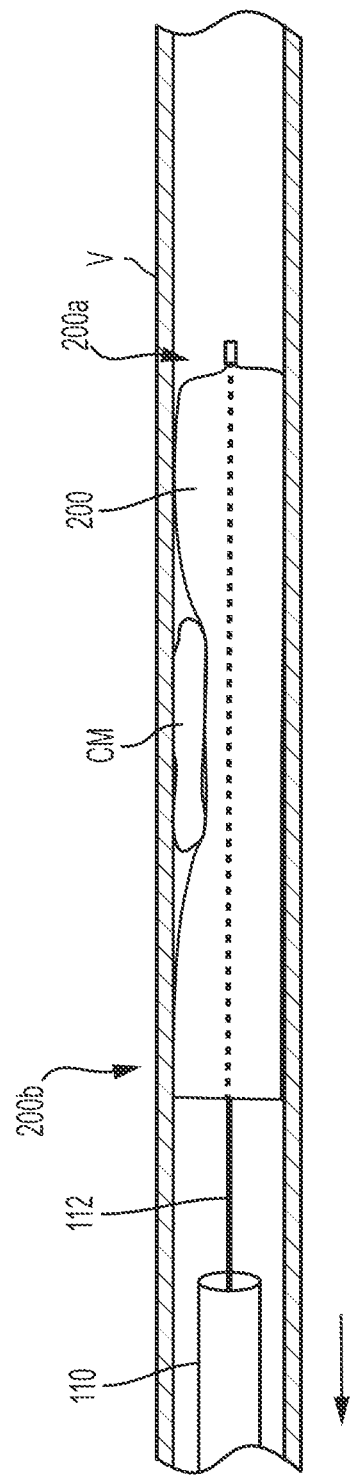

As shown in FIG. 8B, the second catheter 110 may be withdrawn proximally relative to the interventional element 200 to release the interventional element 200, thereby allowing the interventional element 200 to self-expand within the clot material CM into the first position. As the interventional element 200 expands, the interventional element 200 engages the surrounding clot material CM, and in some embodiments may restore or improve blood flow through the clot material CM by pushing open a blood flow path therethrough. In some embodiments, the interventional element 200 is configured to expand into contact with the wall of the vessel V, or the interventional element 200 may expand to a diameter that is less than that of the blood vessel lumen such that the interventional element 200 does not engage the entire circumference of the blood vessel wall.

Once the interventional element 200 has been expanded into engagement with the clot material CM, the interventional element 200 may grip the clot material CM by virtue of its ability to mechanically interlock with the clot material CM. The current generator 102, which is electrically coupled to the proximal end of the elongate member 112, can deliver a current to the interventional element 200 before or after the interventional element 200 has been released from the second catheter 110 into the blood vessel and/or expanded into the clot material CM. The interventional element 200 can be left in place or manipulated within the vessel V for a desired time period while the electrical signal is being delivered. Positive current delivered to the interventional element 200 can attract negatively charged constituents of the clot material CM, thereby enhancing the grip of the interventional element 200 on the clot material CM. This allows the interventional element 200 to be used to retrieve the clot material CM with reduced risk of losing grip on the thrombus or a piece thereof, which can migrate downstream and cause additional vessel blockages in areas of the brain that are more difficult to reach.

Figure 8C:
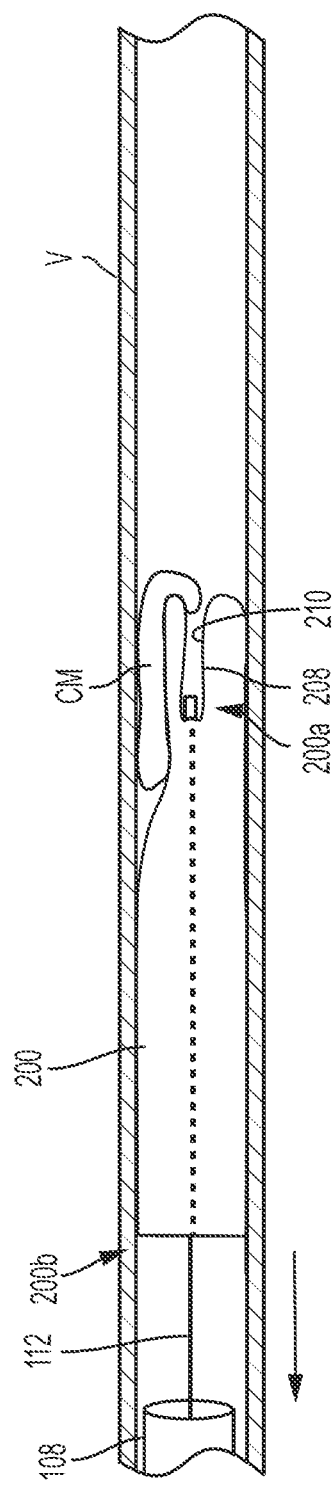
Figure 8D:
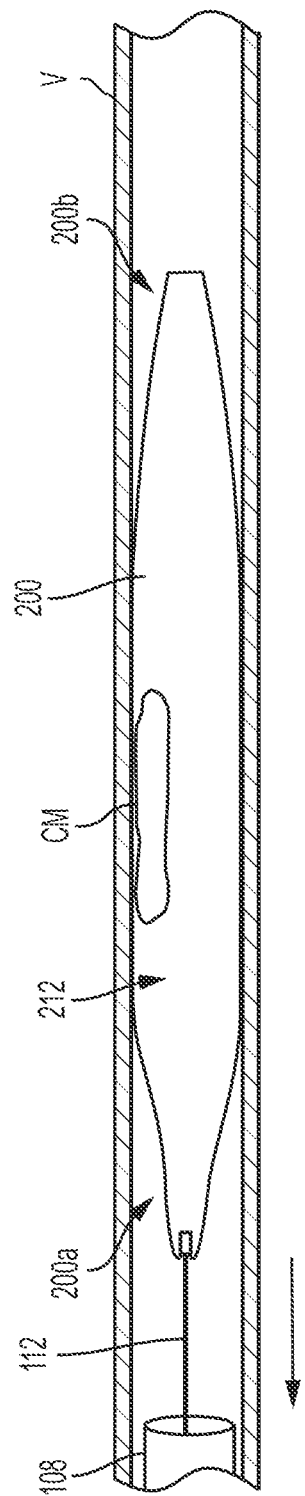

While the interventional element 200 is engaged with the clot material CM, the elongate member 112 can be pulled proximally to evert the interventional element 200. Friction between the blood vessel wall and the mesh wall prevents or resists proximal movement of the free second end portion 200b of the mesh 200 while the first end portion 200a of the mesh 200 moves in a proximal direction with the elongate member 112. In other words, expansion of the mesh 200 provides sufficient friction against the walls of the vessel V to overcome the column strength of the mesh wall, thereby causing the mesh wall to remain in place and/or move less than the first end portion 200a of the mesh 200 so that the mesh wall everts. As shown in FIGS. 8C and 8D, as the mesh wall everts, the first surface 210 of the mesh (on which the clot is adhered) is pulled into the newly formed second interior region 212 and pulls the adhered clot material CM with it.

With continued proximal movement of the elongate member 112, the mesh 200 completely everts from the first position to the second position, thereby encapsulating the clot material CM, as shown in FIG. 8D. The interventional element 200 with the encapsulated clot material CM may continue to be withdrawn proximally until the interventional element 200 with the encapsulated clot material CM is positioned within the first catheter 108 (and/or third catheter). The catheters, interventional element 200, and associated clot material CM may then be withdrawn from the patient. During this retraction, the interventional element 200 can grip the clot material CM electrically and/or electrostatically in addition to encapsulating the clot material CM. (As used herein with reference to gripping or retrieving thrombus or other vascular/luminal material, or to apparatus for this purpose, "electrical" and its derivatives will be understood to include "electrostatic" and its derivatives.) Accordingly, the interventional element 200 can maintain an enhanced or electrically and/or electrostatically enhanced grip on the clot material CM during retraction. In other embodiments, the current generator 102 may cease delivery of electrical signals to the interventional element 200 prior to retraction of the interventional element 200 with respect to the vessel V. In some embodiments, the interventional element 200 and clot material CM form a removable, integrated thrombus-device mass wherein the connection of the thrombus to the device is electrically enhanced, e.g., via the application of current as discussed herein.

One or more optional processes may be performed before, during, and/or after deployment of the interventional element 200. For example, in some methods of the present technology, a guidewire (not shown) may be advanced to the treatment site and pushed through the clot material CM until a distal portion of the guidewire is distal of the clot material CM. The guidewire may be advanced through one or more of the first, second, and/or third catheters, and one or more of the catheters may be advanced over the guidewire. The guidewire may be insulated along at least a portion of its length (e.g., with parylene, PTFE, etc.), with exposed portions permitting electrical communication with the current generator 102 and the interventional element 200. For example, in some embodiments a distal portion of the guidewire may be exposed and the guidewire may be positioned at the treatment site such that the exposed portion of the guidewire is distal of the clot material CM. A proximal end of the guidewire may be coupled to the current generator such that the exposed portion of the guidewire functions as a return electrode. In some embodiments, the guidewire may be coupled to the positive terminal of the power source and the exposed portion functions as a delivery electrode. The guidewire may be used as a delivery or return electrode with any delivery or return electrode carried by any component of the system (e.g., one or more of the first, second, and/or third catheters, the interventional element 200, etc.).

In some methods a fluid may be delivered to the treatment site via the second and/or third catheter while current is being delivered to the interventional element 200. Fluid delivery may occur before or while the interventional element 200 is engaging the thrombus, and may coincide with the entire duration of current delivery or just a portion thereof.

The inventors have observed improved electrically enhanced clot adhesion in the absence of blood flow. As such, it may be especially beneficial to arrest flow (e.g., via a flow arrest element on the first or second catheter 108, 110) while the interventional element 200 is charged, and while expanding the interventional element 200 within the thrombus and/or when withdrawing the thrombus proximally.

Although the presence of blood flow at the treatment site is believed to reduce adhesion between an electrically charged interventional element and a blood clot, the inventors have also observed that infusion of a fluid having a higher ion concentration than blood increases the electrical conductivity at the treatment site, thereby providing an improved environment for electrically enhanced clot adhesion as compared to the presence of blood alone. In some embodiments, infusion of the fluid may occur in the presence of blood flow, or without blood flow present (the latter condition being induced, for example, by inflation of the expandable element on the first catheter 108). Suitable fluids include, for example, saline, contrast solution, and other fluids having a higher ion concentration than blood. Additionally, the delivery of fluid at the treatment site may also reduce new clot formation on the interventional element 200, which may occur in the presence of blood and direct or pulsatile electric current.

In some instances aspiration may be applied to the treatment site via the third catheter. For example, following deployment of the interventional element 200, the second catheter 110 can be retracted and removed from the lumen of the third catheter. The treatment site can then be aspirated via the third catheter, for example via a suction source (such as suction source 115) coupled to a proximal portion of the third catheter. In some embodiments, following expansion of the interventional element 200, the treatment site is aspirated concurrently with supplying electrical energy to the interventional element 200 via the current generator 102. By combining aspiration with the application of electrical energy, any newly formed clots (e.g., any clots formed that are attributable at least in part to the application of electrical energy), or any clot pieces that are broken loose during the procedure, can be pulled into the third catheter, thereby preventing any such clots from being released downstream of the treatment site. As a result, concurrent aspiration may permit the use of higher power or current levels delivered to the interventional element 200 without risking deleterious effects of new clot formation. Additionally, aspiration can capture any gas bubbles formed along the interventional element 200 or other component during application of electrical energy to the interventional element 200, which can improve patient safety during the procedure.

In some embodiments, aspiration is applied while the interventional element 200 is retracted into the third catheter. Aspiration at this stage can help secure the clot material CM within the third catheter and prevent any dislodged portion of the clot material CM from escaping the third catheter and being released back into the vessel V. In various embodiments, the treatment site can be aspirated continuously before, during, or after delivering electrical signals to the interventional element 200 as well as before, during, or after retraction of the interventional element 200 into the third catheter.

At any time before, during, and/or after deployment of the interventional element 200, a flow arrest element may be deployed within the blood vessel proximal of the clot material CM to partially or completely arrest blood flow to the treatment site. For example, the first catheter 108 may be a balloon guide catheter having a balloon at its distal portion. The balloon may be configured to inflate or expand into apposition with the surrounding blood vessel wall, thereby at least partially arresting blood flow distal to the balloon. In some embodiments, the flow arrest element can have other forms or configurations suitable for partially or completely arresting blood flow within the vessel V.

In some methods, the flow arrest element may be deployed at a location along the blood vessel proximal of the clot material CM (for example, at a proximal portion of the internal carotid artery) and may remain inflated as the interventional element 200 is deployed and eventually withdrawn to remove the thrombus. For example, the balloon can block flow from a portion of the artery proximal of the balloon toward the interventional element 200 and treatment area, while the second catheter 110 and third catheter are positioned at the treatment site, while the interventional element 200 is expanded within the clot material CM, while fluid is infused at the treatment site, and while aspiration is applied at the treatment site. In some embodiments, the balloon may be in an unexpanded state and/or deflated at any time throughout the procedure to allow blood flow.

In some embodiments the flow arrest element may be a balloon coupled to the third catheter (such as a distal access catheter). In such embodiments, the first catheter 108 may not include a flow arrest element such that flow arrest is achieved via deployment of the flow arrest element coupled to the third catheter. For example, in such embodiments, the first catheter 108 may be a sheath or support catheter. The balloon may be inflated at a location distal of the distal end of the first catheter 108, closer to the thrombus. In some methods, the flow arrest element may be deflated and inflated several times throughout the procedure.

IV. Select Embodiments of Waveforms for Electrically Enhanced Retrieval

Although the waveforms and other power delivery parameters disclosed herein can be used with the devices and methods described above with respect to FIGS. 1-8D, the waveforms and other parameters are also applicable to other device configurations and techniques. For example, the return electrode can be provided along the catheter wall, as a separate conductive member extending within the catheter lumen, as a needle electrode provided elsewhere in the body, etc. In each of these device configurations, the power delivery parameters and waveforms can be beneficially employed to promote clot adhesion without damaging surrounding tissue. Additionally, although the waveforms and other power delivery parameters disclosed herein may be used for treating a cerebral or intracranial embolism, other applications and other embodiments in addition to those described herein are within the scope of the technology. For example, the waveforms and power delivery parameters disclosed herein may be used to electrically enhance removal of emboli from body lumens other than blood vessels (e.g., the digestive tract, etc.) and/or may be used to electrically enhance removal of emboli from blood vessels outside of the brain (e.g., pulmonary blood vessels, blood vessels within the legs, etc.).

While applying a continuous uniform direct current (DC) electrical signal to positively charge the interventional element and/or catheter can improve attachment to the thrombus, this can risk damage to surrounding tissue (e.g., ablation), and sustained current at a relatively high level may also be thrombogenic (i.e., may generate new clots). For achieving effective clot-grabbing without ablating tissue or generating substantial new clots at the treatment site, periodic waveforms have been found to be particularly useful. Without being bound by theory, the clot-adhesion effect appears to be most closely related to the peak current of the delivered electrical signal. Periodic waveforms can advantageously provide the desired peak current without delivering excessive total energy or total electrical charge. Periodic, non-square waveforms in particular are well suited to deliver a desired peak current while reducing the amount of overall delivered energy or charge as compared to either uniform applied current or square waveforms.

Periodic waveforms that can be used with the devices and methods described above with respect to FIGS. 1-8D, including as pulsed direct current. In some embodiments, the signal comprises a continuous uniform DC electrical signal.

The waveform shape (e.g., pulse width, duty cycle, amplitude) and length of time can each be selected to achieve desired power delivery parameters, such as overall electrical charge, total energy, and peak current delivered to the interventional element and/or catheter. In some embodiments, the overall electrical charge delivered to the interventional element and/or catheter can be between about 30-1200 mC, or between about 120-600 mC. According to some embodiments, the total electrical charge delivered to the interventional element and/or catheter may be less than 600 mC, less than 500 mC, less than 400 mC, less than 300 mC, less than 200 mC, or less than 100 mC.

In some embodiments, the total energy delivered to the interventional element and/or aspiration catheter can be between about 0.75-24,000 mJ, or between about 120-24,000 mJ, or between about 120-5000 mJ. According to some embodiments, the total energy delivered to the interventional element and/or aspiration catheter may be less than 24,000 mJ, less than 20,000 mJ, less than 15,000 mJ, less than 10,000 mJ, less than 5,000 mJ, less than 4,000 mJ, less than 3,000 mJ, less than 2000 mJ, less than 1,000 mJ, less than 900 mJ, less than 800 mJ, less than 700 mJ, less than 600 mJ, less than 500 mJ, less than 400 mJ, less than 300 mJ, or less than 200 mJ, or less than 120 mJ, or less than 60 mJ, or less than 48 mJ, or less than 30 mJ, or less than 12 mJ, or less than 6 mJ, or less than 1.5 mJ.

In some embodiments, the peak current delivered can be between about 0.5-20 mA, or between about 0.5-5 mA. According to some embodiments, the peak current delivered may be greater than 0.5 mA, greater than 1 mA, greater than 1.5 mA, greater than 2 mA, greater than 2.5 mA, or greater than 3 mA.

The duration of power delivery is another important parameter that can be controlled to achieve the desired clot-adhesion effects without damaging tissue at the treatment site or generating new clots. In at least some embodiments, the total energy delivery time can be no more than 1 minute, no more than 2 minutes, no more than 3 minutes, no more than 4 minutes, no more than 5 minutes, or between 1 and 5 minutes. According to some embodiments, the total energy delivery time may be less about 30 seconds, less than about 1 minute, less than about 90 seconds, or less than about 2 minutes. As used herein, the "total energy delivery time" refers to the time period during which the waveform is supplied to the interventional element and/or catheter (including those periods of time between pulses of current).

The duty cycle of the applied electrical signal can also be selected to achieve the desired clot-adhesion characteristics without ablating tissue or promoting new clot formation. In some embodiments, the duty cycle can be between about 5% about 99% or between about 5% to about 20%. According to some embodiments, the duty cycle may be about 10%, about 20%, about 30%, about 40%, or about 50%. In yet other embodiments, a constant current may be used, in which the duty cycle is 100%. For 100% duty cycle embodiments, a lower time or current may be used to avoid delivering excess total energy to the treatment site.

V. Conclusion

Although many of the embodiments are described herein with respect to devices, systems, and methods for treating a cerebral or intracranial embolism, other applications and other embodiments in addition to those described herein are within the scope of the technology. For example, the systems and methods of the present technology may be used to remove emboli from body lumens other than blood vessels (e.g., the digestive tract, etc.) and/or may be used to remove emboli from blood vessels outside of the brain (e.g., pulmonary, abdominal, cervical, or thoracic blood vessels, or peripheral blood vessels including those within the legs or arms, etc.). In addition, the systems and methods of the present technology may be used to remove luminal obstructions other than clot material (e.g., plaque, resected tissue, foreign material, kidney stones, etc.).

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

We claim:

1. A medical device comprising:
an elongate member having a proximal end portion and a distal end portion configured to be positioned proximate a thrombus within a lumen of a blood vessel at a treatment site; and
a mesh having a first end portion coupled to the distal end portion of the elongate member and a second end portion uncoupled from the elongate member, wherein the mesh has an expanded state in which the mesh is eversible between first and second positions and the second end portion is configured to expand and engage a wall of the lumen of the blood vessel, and wherein the mesh is configured to be electrically coupled to an electrical terminal that delivers a current to the mesh to positively charge the mesh and promote adhesion of the thrombus thereto,
wherein, when the device is positioned within the blood vessel lumen and the mesh is in the first position of the expanded state, proximal movement of the elongate member causes the mesh to move from the first position towards the second position.

2. The device of claim 1, wherein:
the elongate member is a first elongate member,
the electrical terminal is a first electrical terminal and is configured to be coupled to the proximal end portion of the first elongate member, and
the device further comprises a second elongate member having a proximal end region configured to be coupled to a second electrical terminal and a distal end region configured to be positioned adjacent the mesh at the treatment site.

3. The device of claim 2, wherein the first electrical terminal is positive and the second electrical terminal is negative.

4. The device of claim 3, wherein, when the mesh is in the presence of an electrolytic medium and voltage is supplied to the first and second electrical terminals, current flows from the mesh to the second elongate member.

5. The device of claim 2, wherein the first elongate member comprises an electrically conductive member configured to carry electrical current between the first electrical terminal and the mesh, and wherein the first elongate member further comprises an insulative material at least partially surrounding the electrically conductive member.

6. The device of claim 1, wherein the mesh is in electrical communication with the elongate member.

7. The device of claim 1, wherein the mesh comprises a plurality of braided metallic wires.

8. The device of claim 1, wherein, when the mesh is in the first position, at least a portion of a length of the mesh surrounds a portion of the elongate member.

9. The device of claim 1, wherein, when the mesh is in the second position, an entire length of the mesh is distal of the elongate member.

10. The device of claim 1, wherein the mesh is closed at the first end portion and open at the second end portion.

11. The device of claim 1, wherein the first end portion of the mesh is fixed relative to the elongate member and the second end portion is free to move relative to the elongate member.

12. The device of claim 1, wherein when in the first position, the mesh is configured to be positioned adjacent to the thrombus such that the mesh is expanded into engagement with the thrombus.

13. A medical device comprising:
a first elongate member having a proximal region configured to be coupled to a first electrical terminal and a distal region configured to be positioned adjacent a thrombus in a blood vessel;
a second elongate member having a proximal end portion configured to be coupled to a second electrical terminal and a distal end portion; and
a mesh having a first end portion coupled to the distal end portion of the second elongate member and a second end portion uncoupled from the first and second elongate members, the mesh being movable between (a) a first position in which the second end portion is proximal of the first end portion, and (b) a second position in which the second end portion is distal of the first end portion, wherein when the device is positioned within the blood vessel and the mesh is in the first position, proximal movement of the second elongate member causes the mesh to move from the first position towards the second position.

14. The device of claim 13, wherein the mesh is in electrical communication with the second elongate member.

15. The device of claim 13, wherein the first elongate member is an elongate shaft defining a lumen and the second elongate member is configured to be slidably received within the lumen.

16. The device of claim 13, wherein the first electrical terminal is positive and the second electrical terminal is negative.

17. The device of claim 13, wherein, when the mesh is in the presence of an electrolytic medium and voltage is supplied to the first and second electrical terminals, current flows from the mesh to the first elongate member.

18. The device of claim 13, wherein when in the first position, the mesh is configured to be positioned adjacent to the thrombus such that the mesh is expanded into engagement with the thrombus.

19. A method for retrieving clot material from within a vessel lumen of a patient, the method comprising:
   positioning a mesh within the vessel lumen at or near the clot material, the mesh having a first end portion coupled to an elongate member and a second end portion uncoupled from the elongate member;
   expanding the mesh within the vessel lumen into a first position such that at least a portion of the mesh expands into contact with the clot material, wherein the first end portion of the mesh is distal of the second end portion of the mesh when the mesh is in the first position, and wherein the second end portion is configured to expand and engage a wall of the vessel lumen;
   promoting adhesion of the clot material to the mesh by delivering an electrical signal to the mesh; and
   pulling the elongate member proximally, thereby transforming the mesh into a second position in which the second end portion of the mesh is distal of the first end portion such that the mesh encapsulates at least a portion of the clot material.

20. The method of claim 19, wherein the electrical signal is positively charged and delivered to the mesh while the elongate member pulls the mesh proximally, and wherein the method further comprises ceasing delivery of the electrical current to the mesh after a time period.

* * * * *